(12) United States Patent
Hlavenka et al.

(10) Patent No.: US 8,735,849 B2
(45) Date of Patent: May 27, 2014

(54) DETECTOR FOR USE IN CHARGED-PARTICLE MICROSCOPY

(75) Inventors: Petr Hlavenka, Brno (CZ); Marek Uncovsky, Brno (CZ)

(73) Assignee: FEI Company, Hillsboro, OR (US)

( * ) Notice: Subject to any disclaimer, the term of this patent is extended or adjusted under 35 U.S.C. 154(b) by 220 days.

(21) Appl. No.: 13/396,171

(22) Filed: Feb. 14, 2012

(65) Prior Publication Data

US 2012/0205539 A1    Aug. 16, 2012

Related U.S. Application Data

(60) Provisional application No. 61/442,546, filed on Feb. 14, 2011.

(30) Foreign Application Priority Data

Feb. 14, 2011    (EP) .................................... 11154322

(51) Int. Cl.
*H01J 37/244*    (2006.01)

(52) U.S. Cl.
USPC .................................... 250/397; 313/103 CM

(58) Field of Classification Search
USPC .......... 250/310, 311, 307, 396 R, 492.2, 397
See application file for complete search history.

(56) References Cited

U.S. PATENT DOCUMENTS

| | | | |
|---|---|---|---|
| 4,317,036 A * | 2/1982 | Wang | 378/45 |
| 4,363,969 A * | 12/1982 | Ong | 250/367 |
| 5,945,672 A | 8/1999 | Knowles et al. | |
| 5,990,483 A * | 11/1999 | Shariv et al. | 250/397 |
| 6,858,912 B2 | 2/2005 | Marshall et al. | |
| 6,946,654 B2 | 9/2005 | Gerlach et al. | |
| 7,227,142 B2 | 6/2007 | Parker | |
| 7,718,979 B2 | 5/2010 | Knowles | |
| 7,845,245 B2 | 12/2010 | Hayles et al. | |
| 7,851,769 B2 | 12/2010 | Schmid et al. | |
| 8,068,896 B2 * | 11/2011 | Daghighian et al. | 600/436 |
| 8,314,410 B2 * | 11/2012 | Straw et al. | 250/492.3 |
| 8,330,115 B2 * | 12/2012 | Frank | 250/390.01 |
| 8,334,512 B2 | 12/2012 | Luecken et al. | |

(Continued)

FOREIGN PATENT DOCUMENTS

| | | |
|---|---|---|
| EP | 2381236 | 10/2011 |
| EP | 2521157 | 11/2012 |

OTHER PUBLICATIONS

Unknown, "MPPC(R) (Multi-pixel photon Counter) S10362-33 series S10931 series." www.hamatsu.com.

(Continued)

*Primary Examiner* — Nikita Wells
*Assistant Examiner* — Johnnie L Smith
(74) *Attorney, Agent, or Firm* — Scheinberg & Associates, PC; Michael O. Scheinberg; James Wolfe

(57) ABSTRACT

A method of investigating a sample using a charged-particle microscope is disclosed. By directing an imaging beam of charged particles at a sample, a resulting flux of output radiation is detected from the sample. At least a portion of the output radiation is examined using a detector, the detector comprising a Solid State Photo-Multiplier. The Solid State Photo-Multiplier is biased so that its gain is matched to the magnitude of output radiation flux.

21 Claims, 4 Drawing Sheets

(56) References Cited

U.S. PATENT DOCUMENTS

| | | | |
|---|---|---|---|
| 8,338,782 B2 | 12/2012 | Leucken et al. | |
| 8,350,213 B2 * | 1/2013 | Wang et al. | 250/310 |
| 8,350,218 B2 * | 1/2013 | Thon et al. | 250/361 R |
| 2003/0010913 A1 | 1/2003 | Essers | |
| 2006/0240586 A1 | 10/2006 | Kobayashi et al. | |
| 2010/0198061 A9 * | 8/2010 | Daghighian et al. | 600/436 |
| 2010/0245809 A1 | 9/2010 | Andreou et al. | |
| 2010/0294931 A1 | 11/2010 | Zarchin et al. | |
| 2011/0215241 A1 * | 9/2011 | Wang et al. | 250/307 |
| 2011/0240865 A1 | 10/2011 | Frach et al. | |
| 2011/0248164 A1 * | 10/2011 | Straw et al. | 250/307 |
| 2012/0032078 A1 | 2/2012 | Stekelenburg et al. | |
| 2012/0037802 A1 | 2/2012 | Kneedler | |
| 2012/0205539 A1 | 8/2012 | Hlavenka et al. | |
| 2012/0256085 A1 | 10/2012 | Otten et al. | |
| 2013/0032713 A1 | 2/2013 | Barbi et al. | |

OTHER PUBLICATIONS

Henseler, Debora et. al., "SiPM performance in PET applications: an experimental and theoretical analysis," IEEE Nuclear Science Symposium Conference Record, Nov. 2009, pp. 1941-1948, vol. 28, No. 1.

Johnson, Erik B. et. al., "Energy resolution in CMOS SSPM detectors coupled to an LYSO scintillator," IEEE Transaction on Nuclear Science, Jun. 2009, pp. 1024-1032, vol. 56, No. 3.

Lightfoot, P.K. et. al., "Characterisation of a silicon photomultiplier device for applications in liquid argon based neutrino physics and dark matter searches," Journal of Instrumentation, Oct. 6, 2008, pp. 1-20, vol. 10, No. 10, IOP Publishing Ltd and SISSA.

Renker, D., "Geiger-mode avalanche photodiodes for Cherenkov detectors," Journal of Instrumentation, Institute of Physics Publishing, Jan. 4, 2010, pp. 13, vol. 5.

Verghese, Simon, et. al., "GaN avalanche photodiodes operating in linear-gain mode and geiger mode," IEEE Transactions on Electron Devices, Mar. 2001, pp. 502-511, vol. 48, No. 3.

Wang, Gin-Chung, et.al., "Solid-state photomultipliers for biomedical imaging applications," Proc. SPIE, Feb. 12, 2009, pp. 11, vol. 7182.

* cited by examiner

DETECTOR FOR USE IN CHARGED-PARTICLE MICROSCOPY

This Application claims priority from U.S. Provisional Application 61/442,546, filed Feb. 14, 2011, which is hereby incorporated by reference.

TECHNICAL FIELD OF THE INVENTION

The invention relates to a method of investigating a sample using a charged-particle microscope.

BACKGROUND OF THE INVENTION

Electron microscopy is a well-known technique for imaging microscopic objects. The basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (that additionally employ a "machining" beam of ions, allowing supportive activities such as ion-beam milling or ion-beam-induced deposition, for example). In traditional electron microscopes, the imaging beam is "on" for an extended period of time during a given imaging session; however, electron microscopes are also available in which imaging occurs on the basis of a relatively short "flash" or "burst" of electrons, such an approach being of potential benefit when attempting to image moving samples or radiation-sensitive specimens, for example.

In current electron microscopes [and other charged-particle microscopes], use is often made of a detector that employs an evacuated photo-multiplier tube (PMT) in conjunction with a scintillator. In such a set-up, output electrons emanating from the sample move toward and strike the scintillator (which will often be maintained at an accelerating potential of the order of a few kV with respect to the sample), thus causing the production of photonic radiation (i.e. electromagnetic radiation, such as visible light) that, in turn, is directed (e.g. with the aid of a light guide) to a photo-emissive cathode of the PMT, from which it triggers the ejection of one or more photoelectrons. Each such photoelectron traverses a series of high-voltage dynodes—each of which emits a plurality of electrons for each impinging electron (cascade effect)—so that a greatly augmented number of electrons eventually leaves the last dynode and strikes a detection anode, producing a measurable electric current or pulse. The cathode, dynodes and anode are all located in an evacuated vitreous tube.

This known detector set-up (often referred to as an Everhart-Thornley detector) has certain drawbacks. For example, the vitreous tube of the PMT is necessarily quite bulky, seeing as it has to accommodate multiple electrodes in a specific mutual configuration, and has to support high internal vacuum. Such bulkiness is exacerbated by the fact that each electrode requires an electrical connection through the wall of the vitreous tube to the tube's exterior, where it is connected via an electrical cable to a high-voltage source (typically operating in the kV range). In addition, a light guide between the scintillator and the PMT may necessarily be quite long (e.g. due to spatial restrictions in placement of the PMT), and this will generally lead to some degree of signal loss. Moreover, the very principle of operation of the PMT results in a relatively large ultimate electrical current for each electron that strikes the scintillator; consequently, in a scenario in which irradiation of a sample by an imaging beam produces a relatively large flux of output radiation from the sample, this can result in an excessive electrical current at the anode of the PMT. To mitigate this effect, one can attempt to attenuate the input to the PMT in some way, e.g. by making the employed scintillator less sensitive, but such action will generally tend to complicate the detector set-up even further.

Accordingly, there is a need to provide a radically alternative detection scenario to that set forth above.

SUMMARY OF THE INVENTION

The invention relates to a method of investigating a sample using a charged-particle microscope. By directing an imaging beam of charged particles to a sample, a flux of output radiation emanates from the sample. The output radiation is detected and examined using a Solid State Photo-Multiplier.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Figure 1:
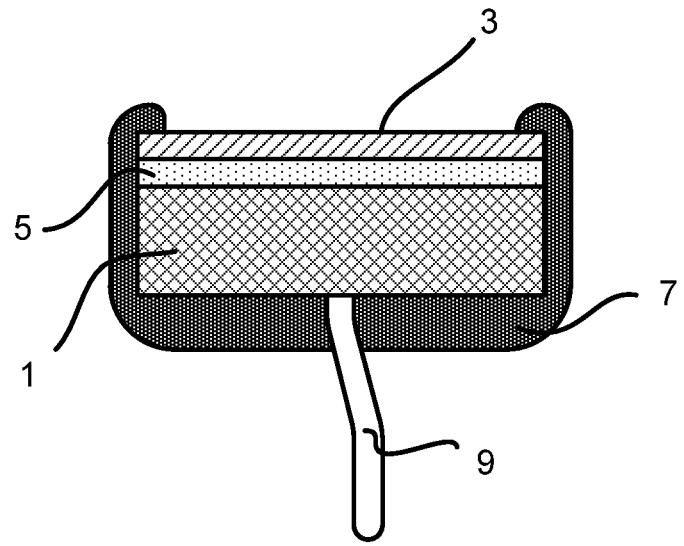
FIG. 1 shows a cross-sectional view of a particular embodiment of a composite Multi-Pixel Photon Counter-based detector that, in accordance with the present invention, can be used in a charged-particle microscope.

In research leading to the invention, the inventors realized that the bulkiness of detectors based on evacuated PMTs was a bottleneck to the ongoing desire to develop more compact and/or innovative types of electron microscope [and other types of charged-particle microscope]. The inventors therefore embarked upon a systematic engineering project to develop a totally new type of detector for use in electron microscopy, with the aim of overcoming the seemingly unassailable hurdle imposed by said bottleneck.

To start off with, the inventors turned their attention to photodiodes (PDs), which have the advantages of being compact and of requiring only a relatively low operating voltage, and the additional merit of being comparatively inexpensive. However, a drawback of PDs is that they do not have a significant/satisfactory amplification effect, making them relatively unsuitable for detection of weak signals. To overcome this drawback, the inventors considered using so-called avalanche photodiodes (APDs), which employ an electrical bias to produce an "avalanche" of electrons for a given triggering photon. However, although these devices did produce an amplification effect, it was considered to be too weak for many applications in electron microscopy.

Next, the inventors performed experiments with Geiger-APDs (or GAPDs), which are APDs operated in so-called Geiger mode, whereby the employed operating bias is greater than the breakdown voltage of the diode concerned, causing a breakdown shower of electrons (self-sustained discharge) for a given triggering photon. However, just like a catapult that needs to be rewound after firing, a GAPD needs to "quench" and "recharge" after each triggering event, and this process requires a span of time that is referred to as the "recovery time" or "dead time" of the device, and is typically in the nanosecond range. If a photon impinges on the device during this dead time, the device cannot produce the desired discharge in response thereto, as a result of which the photon in question will go undetected. Consequently, such a set-up would not lend itself to the detection of relatively high fluxes of photons.

The inventors next postulated that the disadvantageous effect of the above-mentioned dead time could be circumvented if one were to use an array of detection diodes, the associated argumentation being that, at any given time, some of the diodes in such an array would be experiencing their dead time, but others would be trigger-ready; consequently, in general, any photon arriving at the array would always be met by at least some diodes that were ready and able to trigger, so that such a photon would have an increased probability of being detected. The inventors realized that, in order to offer optimum placement versatility, such an array would need to be relatively compact, and preferably in the form of an integrated (i.e. on-chip) device. However, prior to taking steps to contact a semiconductor foundry to discuss the design and manufacture of such an integrated device, they discovered by coincidence that, in the field of high-energy particle physics experimentation (such as conducted at CERN, FermiLab, etc.), researchers hunted elusive and exotic sub-atomic particles using very sensitive pulse-counting devices called Multi-Pixel Photon Counters (also known by names such as Solid State Photo-Multipliers (SSPMs), Silicon Photo-Multiplier (SiPMs), on-chip pixelated APD arrays, etc.), which were essentially on-chip arrays of the order of about $10^3$-$10^4$ APDs with shared/common detection circuitry, and turned out to be commercially available, e.g. from the firm Hamamatsu in Japan under the name MPPC®. It is noted that also Multi-Pixel Photon Counters with between 10 and 1000 APD's are available.

It was felt ab initio that, in view of the very disparate needs of high-energy particle physics researchers as compared to those of electron microscopy engineers, such Multi-Pixel Photon Counters would not offer satisfactory performance in an electron microscope; however, it was considered to be a fruitful exercise to at least undertake to perform some investigative experiments with them.

As expected, preliminary experiments suggested that the Multi-Pixel Photon Counters were unsuitable for use as detectors in electron microscopy. Their very name—"photon counters"—indicates that they are intended to deal with very low detection fluxes, and they were indeed found to be severely saturated at even moderate detection fluxes, such as commonly occur in electron microscopy.

However, in a chance event, the inventors discovered that, when a test Multi-Pixel Photon Counter was operated at bias levels below the specifications stipulated by the manufacturer, it demonstrated a much lower gain. This phenomenon caught the interest of the inventors, and they embarked upon a full series of experiments to investigate it further. Eventually, they were surprised to observe that, when a Multi-Pixel Photon Counter was operated within a relatively narrow voltage band outside of spec, its gain varied in a reproducible manner—without saturation effects—through several orders of magnitude, according to a weak "S-shaped" response curve; for example, for a specific MPPC specimen having a specified operating voltage above 74 V, it was found that the gain varied smoothly through four orders of magnitude as a function of applied bias in the range ~69-73 V.

The inventors seized upon this realization and, according to the present invention, conceived a successful implementation of a Multi-Pixel Photon Counter as a detector for electron microscopy [and, ultimately, other types of charged-particle microscopy]. According to this implementation, the operating bias of the Multi-Pixel Photon Counter (i.e. on-chip pixelated Geiger-mode Avalanche Photodiode array, Solid State Photomultiplier (SSPM), etc.) is carefully adjusted so as to endow it with a gain value that is matched to a particular detection circumstance; for example, for situations in which a low flux of output radiation is expected to emanate from a sample, a relatively large bias can be applied to the Multi-Pixel Photon Counter (thus giving it relatively high gain) whereas, under circumstances in which a higher flux of output radiation is expected to emanate from the sample, the gain of the Multi-Pixel Photon Counter can be appropriately "choked" by operating it at a relatively low bias. The exact bias to be applied to the Multi-Pixel Photon Counter so as to realize a desired gain can be determined on the basis of a bias/gain calibration curve drawn up prior to using the Multi-Pixel Photon Counter in an electron microscope [or other charged-particle microscope].

Despite the fact that a Multi-Pixel Photon Counter used in this manner is operating outside the specifications stipulated by its manufacturer, the inventors have observed that it nevertheless generally demonstrates acceptable temperature stability, signal-to-noise ratio (SNR) and reproducibility; although the SNR tends to be significantly lower (the noise significantly larger) than typically achieved from an evacuated PMT or from a Multi-Pixel Photon Counter operating within specifications, it does not tend to impede measurement accuracy to any great extent.

The novel detector developed by the inventors in accordance with the present invention is much smaller than an evacuated PMT (or other conventional detector types used in charged-particle microscopy), and operates at a much lower voltage. Accordingly, it can be placed in locations and used in circumstances that are not possible in the case of (inter alia) evacuated PMT-based detectors, thus opening the door to a whole scala of new types of charged-particle microscope. For example:

In a charged-particle microscope according to the present invention, the novel detector can be located in very close proximity to the sample being investigated, since the detector is much more compact than an evacuated PMT. An advantage of such a configuration is that it generally allows the detector to more efficiently capture output radiation emanating from the sample. Specifically, a Multi-Pixel Photon Counter can be placed very close to an associated scintillator (located adjacent to a sample), removing the need for a relatively long light guide between the two, thus helping to curtail signal loss.

The detector according to the current invention can be wholly located within the particle-optical column (objective lens) of a charged-particle microscope. Such a configuration has hitherto been difficult in the case of evacuated PMT-based detection, predominantly because of the bulk associated with the evacuated PMT, but also because of the electric fields associated therewith. An "in-lens" detector configuration has the advantage of allowing greater freedom of choice as regards the so-called "working distance" of the microscope; in particular, one can realize a shorter working distance and, accordingly, reduce the effect of lens aberrations (which scale with working distance).

Attendant to the previous example, one can comprise the current invention in a so-called "immersion lens", i.e. a set-up in which the sample resides in an electric or magnetic field of the lens. Since output electrons emanating from such a sample cannot escape from the lens to an external detector, the detector will instead have to be located within the lens, and will have to be capable of operating satisfactorily in an electric/magnetic field. The detector arrangement according to the current invention is compatible with these requirements.

As set forth above, evacuated PMTs tend to "overload" when used to measure high fluxes of output radiation emanating from a sample. However, the detector according to the present invention, which has its gain tuned according to the expected detection flux, does not suffer from this problem.

The invention lends itself to application in charged-particle microscopy in which so-called cathodoluminescence (CL) is measured. Because the detector according to the invention is so compact and, accordingly, can be placed close to the sample, it affords a larger angular aperture to capture CL photons.

In a given embodiment of a charged-particle microscope according to the invention, the detector additionally comprises a scintillator. In such a scenario, the Multi-Pixel Photon Counter discussed above acts as a measuring element and the scintillator acts as a converting element, serving to convert output electrons emanating from the sample into photons that then impinge upon the measuring element.

In an alternative scenario (e.g. when measuring CL radiation), the Multi-Pixel Photon Counter discussed above is used to directly detect output photons emanating from the sample, which can be done without the intermediary of a converting scintillator.

Embodiment 1

Multi-Pixel Photon Counters are commercially available from firms such as Hamamatsu Photonics KK, Japan (for example). A Multi-Pixel Photon Counter typically comprises a 2-dimensional array of several hundred or several thousand individual Geiger-APDs, integrated on a small chip. Such a chip typically has lateral dimensions of the order of about 3×3 $mm^2$. In some cases, such chips can be housed in a (metal, ceramic or plastic) canister provided with electrical connection leads; however, such a canister is not necessary, and "naked" Multi-Pixel Photon Counter chips are also commercially available.

To appreciate the scale of such Multi-Pixel Photon Counter chips, the following comparison is merited. As a reference, an evacuated PMT (photomultiplier tube) with a (typical) diameter of the order of about 2½ cm and a (typical) length of the order of about 10 cm will have a volume of the order of about 80 $cm^3$. In contrast, a canister as referred to above will typically have a volume of the order of about 1 $cm^3$ or less, making it almost a hundred times smaller than said evacuated PMT. On the other hand, a "naked" Multi-Pixel Photon Counter chip mounted on a thin substrate (such as a sheet of glass, for example) will typically have a volume of the order of about 3×3×1 $mm^3$=9 $mm^3$=0.009 $cm^3$, making it approximately ten thousand times smaller than an evacuated PMT.

This scale difference allows a very significant reduction in detector size as compared to evacuated PMTs (or other types of detector, such as conventional solid state detectors, for example), thus allowing Multi-Pixel Photon Counter -based detectors to be located in confined spaces that are too cramped for an evacuated PMT (or other known detector types). Moreover, because Multi-Pixel Photon Counters are so small, and also very much cheaper than prior-art detectors, it becomes possible to employ several of them in unison—which allows more versatile detection possibilities as compared to the use of a single, bulky detector; for example, one could surround a sample by a whole "cloud" of such Multi-Pixel Photon Counter detectors, allowing output radiation emanating from the sample to not only be detected, but also to be angularly/directionally resolved.

It is worth mentioning that such a multitude of detectors can be formed from completely separated chips, but can also be integrated on one die, preferably with a hole in the middle for passing the beam of charged particles to the sample.

In addition to these merits as regards size, cost and novel measurement configurations, a detector according to the invention has a further advantage: because a Multi-Pixel Photon Counter is comprised of APDs, its operation is not impeded to any significant extent by magnetic fields in its vicinity. On the other hand, since the operation of (for example) an evacuated PMT relies on the use of accelerating electrostatic fields generated between electrode pairs, its functioning can be detrimentally affected by environmental magnetic fields of significant magnitude. Because a Multi-Pixel Photon Counter is relatively insensitive to electric/magnetic fields, it can be successfully deployed in locations that are precluded to an evacuated PMT; for example, it can be located within a particle-optical lens.

The inventors have surprisingly shown that a Multi-Pixel Photon Counter, when operated in a particular manner outside the manufacturer's specifications, can be successfully used to measure an incoming radiative flux across about 5 decades of magnitude, without being impeded by saturation effects, and with satisfactory reproducibility and signal-to-noise ratio. To this end, the Multi-Pixel Photon Counter is connected to a power supply providing an adjustable electrical bias, and this bias is varied so as to adjust a gain value of the Multi-Pixel Photon Counter. By appropriately choosing the employed bias value, one can match the device gain to the (expected or observed) magnitude of the incoming radiative flux to be measured, creating a scenario whereby the Multi-Pixel Photon Counter consistently operates below a saturation threshold for the device (i.e. up to an acceptable saturation level).

In general, the thermal sensitivity of a Multi-Pixel Photon Counter operated in this manner was found by the inventors to be acceptable. However, to the extent that, in a particular application, the thermal sensitivity is considered to be a more critical issue, one can always resort to one or both of the following steps:

Prevention, whereby one endeavors to keep the temperature of the Multi-Pixel Photon Counter as stable as possible;

Correction, whereby the temperature of/at the Multi-Pixel Photon Counter is continually monitored, and any changes therein are compensated therefor by appropriate (slight) adjustments to the applied bias value.

In respect of this novel application of a Multi-Pixel Photon Counter as a detector in a charged-particle microscope, the following should be noted:

A Multi-Pixel Photon Counter can be used according to the invention to directly measure incoming photonic radiation, such as CL radiation; such measurement does not require the intermediary of a converting element such as a scintillator.

A Multi-Pixel Photon Counter can also be used in accordance with the invention to indirectly measure incoming particulate radiation, by employing a scintillator to convert a flux of particles (such as secondary or backscattered electrons, or ions) into photons, which then impinge upon the Multi-Pixel Photon Counter.

The next Embodiment will be devoted to a particular set-up that lends itself to such indirect measurement.

Embodiment 2

FIG. 1 shows a cross-sectional view of a particular embodiment of a composite Multi-Pixel Photon Counter-based detector that, in accordance with the present invention, can be used in a charged-particle microscope. The figure shows a (naked) Multi-Pixel Photon Counter chip 1 that is separated from a scintillator 3 via an interposed layer 5 of optically transparent material, such as glass or a suitable type of grease, for instance. The scintillator 3 may comprise a YAG (Yttrium Aluminium Garnet) crystal, for example.

The interposed (light guide) layer 5 serves to (partially) match the refractive indices of the scintillator 3 and Multi-Pixel Photon Counter 1, and also to electrically isolate them from one another. In use, the Multi-Pixel Photon Counter 1 will be operated at a relatively low voltage, whereas the scintillator 3 will often be maintained at a relatively high electrical potential (typically of the order of kV). To prevent arc-over, the sandwiched assembly 3, 5, 1 is partially encapsulated in a molded insulating jacket 7, which may comprise a (vacuum-compatible) substance such as silicon rubber or an epoxy resin, for example. This jacket 7 has a form/shape that leaves a substantial portion of a face of the scintillator 3 exposed to incoming particle radiation. If desired, this exposed face of the scintillator 3 (remote from the Multi-Pixel Photon Counter 1) may be thinly metallized, so as to reflect photons generated in the scintillator 3 towards the Multi-Pixel Photon Counter 1. Such a metallization is often also desired to form a conductive surface on the (often insulating) scintillator, as otherwise charging could occur.

Also shown in the figure is a signal cable 9, which carries the output signal from the Multi-Pixel Photon Counter 1 to a controller (not depicted).

Embodiment 3

Figure 2:
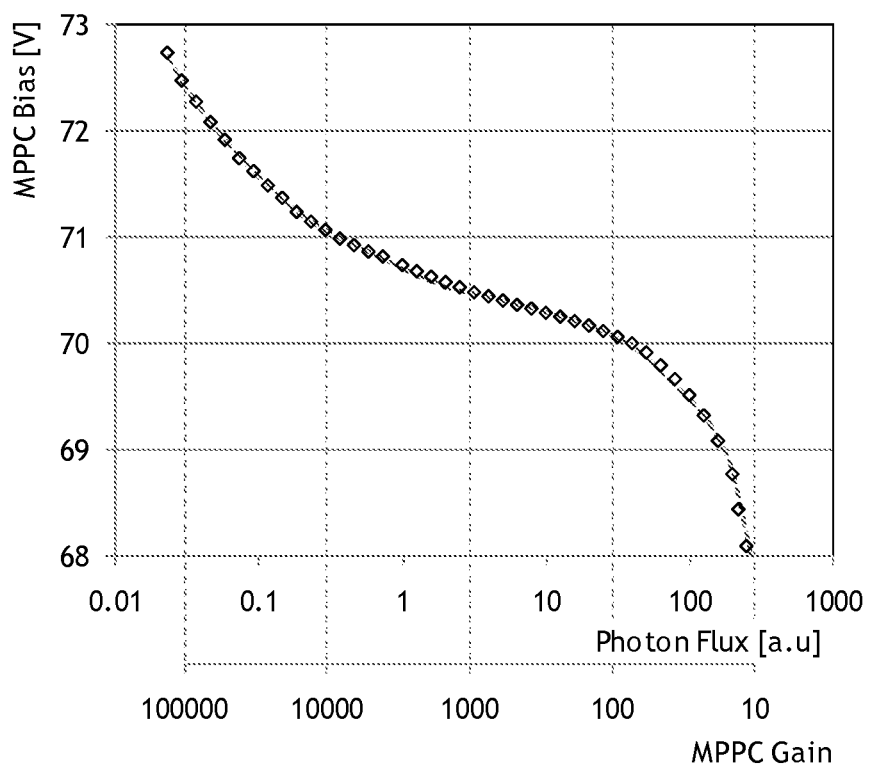
FIG. 2 shows a graph of gain versus bias for a particular Multi-Pixel Photon Counter, obtained using the insights underlying the current invention and exploitable in a detector for use in a charged-particle microscope according to the current invention.

FIG. 2 shows a graph of gain versus bias for a particular embodiment of an Multi-Pixel Photon Counter, obtained using the insights underlying the current invention and exploitable according to the invention in a detector for application in a charged-particle microscope. In this specific case, the Multi-Pixel Photon Counter is a type/model S10931-25P, obtainable from Hamamatsu Photonics KK, Japan, and containing a 2-dimensional array of 14400 Geiger-APDs in a 3×3 mm$^2$ die (chip) area. For this particular Multi-Pixel Photon Counter, the manufacturer specified an operating voltage of approximately 74V; however, for other Multi-Pixel Photon Counters, manufacturers can specify different operating voltages (depending inter alia on the details of the integrated circuit design in the MPPC in question).

In a test associated with the present invention, the Multi-Pixel Photon Counter in question was subjected to an out-of-spec operating voltage. The graph in FIG. 2 shows the surprising results, whereby, when the Multi-Pixel Photon Counter is operated within a relatively narrow sub-spec voltage band, its gain is observed to vary in a reproducible manner—without saturation effects—through several orders of magnitude, according to a weak "S-shaped" response curve.

The inventors think that the observed behavior of the Multi-Pixel Photon Counter may be explained as follows.

At different positions in the bias/gain curve, the mechanism by which the Multi-Pixel Photon Counter creates gain changes.

At bias values ≥74V, the device is in nominal photon counting mode, as developed by the manufacturer.

Below that, e.g. in the range ~74-70V, avalanche firing probability decreases, an avalanche has lower gain, and recovery time is shorter; consequently, the device can handle a higher incoming radiation rate without saturation, at a lower gain.

At yet lower bias values, e.g. ~70-40V, the device no longer operates in Geiger mode, but instead shows normal APD characteristics: no saturation effect, internal gain ~10-100 (electrons arising from secondary generation, but not from breakdown effects).

At even lower bias values, e.g. ~40-0V, there is no internal gain. The device acts as normal photodiode, whereby one photon generates one electron-hole pair.

In the illustrated graph, a spline fit has been made to the depicted data points. This fit can subsequently be used to predict what bias value to use in order to optimally set the gain of the Multi-Pixel Photon Counter to a given value, allowing it to deal with a measured or expected flux of incoming radiation without exceeding an acceptable saturation level. If such an incoming flux is expected to be very weak, the Multi-Pixel Photon Counter can be used at (or close to) the manufacturer-stipulated operating voltage, so that it behaves as a pulse counter; on the other hand, if an incoming flux is expected to be very strong, the Multi-Pixel Photon Counter can be operated at a very low bias, taking it out of Geiger mode and into APD or PD mode, if required (see previous paragraph).

Embodiment 4

Figure 3:
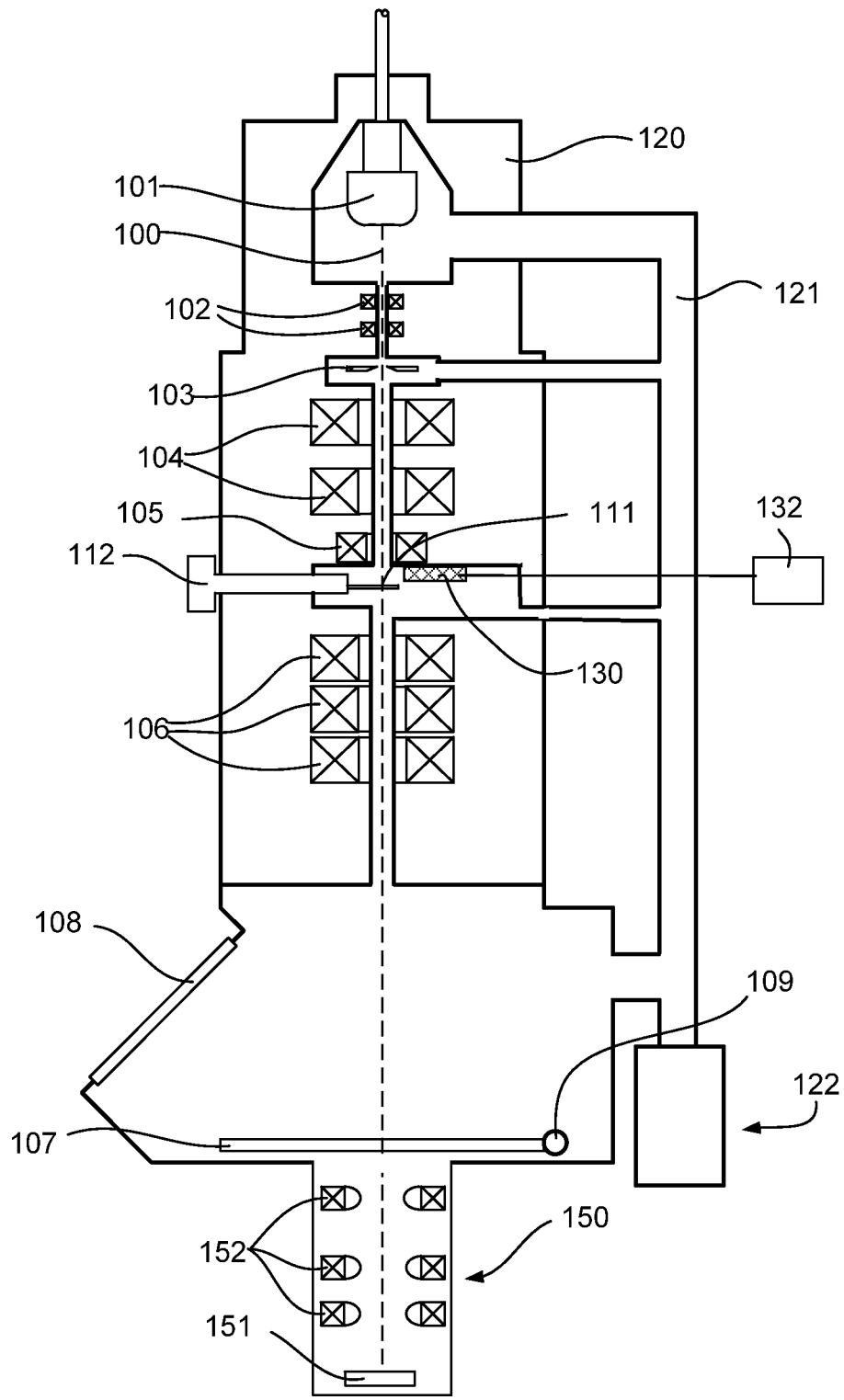
FIG. 3 shows a longitudinal cross-sectional view of a particular embodiment of a charged-particle microscope—in this specific case a TEM—according to the current invention.

FIG. 3 renders a longitudinal cross-sectional view of a particular embodiment of a TEM according to the current invention.

The depicted TEM comprises a vacuum housing 120 that is evacuated via tube 121 connected to a vacuum pump 122. A particle source in the form of an electron gun 101 produces a beam of electrons along a particle-optical axis (imaging axis) 100. The electron source 101 can, for example, be a field emitter gun, a Schottky emitter, or a thermionic electron emitter. The electrons produced by the source 101 are accelerated to an adjustable energy of typically 80-300 keV (although TEMs using electrons with an adjustable energy of 50-500 keV, for example, are also known). The accelerated electron beam then passes through a beam limiting aperture/diaphragm 103 provided in a platinum sheet. To align the electron beam properly to the aperture 103, the beam can be shifted and tilted with the aid of deflectors 102, so that the central part of the beam passes through the aperture 103 along axis 100. Focusing of the beam is achieved using magnetic lenses 104 of the condenser system, together with (part of the) objective lens 105. Deflectors (not depicted) are used to centre the beam on a region of interest on a sample 111, and/or to scan the beam over the surface of the sample.

The sample 111 is held by a sample holder 112 in such a manner that it can be positioned in the object plane of objective lens (particle-optical column) 105. The sample holder 112 may be a conventional type of sample holder for holding a static sample in a containment plane; alternatively, the sample holder 112 can be of a special type that accommodates a moving sample in a flow plane/channel that can contain a stream of liquid water or other solution, for example.

The sample 111 is imaged by a projection system comprising lenses 106 onto fluorescent screen 107, and can be viewed through a window 108. The enlarged image formed on the screen typically has a magnification in the range $10^3$x-$10^6$x, and may show details as small as 0.1 nm or less, for example. The fluorescent screen 107 is connected to a hinge 109, and can be retracted/folded away such that the image formed by the projection system 106 impinges upon primary detector 151. It is noted that, in such an instance, the projection system 106 may need to be re-focused so as to form the image on the primary detector 151 instead of on the fluorescent screen 107. It is further noted that the projection system 106 will generally additionally form intermediate images at intermediate image planes (not depicted).

The primary detector 151 may, for example, comprise a Charge Coupled Device (CCD) for detecting impinging electrons. As an alternative to electron detection, one can also use a CCD that detects light—such as the light emitted by a Yttrium Aluminium Garnet (YAG) crystal (for example) that is bonded to the CCD, or connected thereto by optical fibres (for example). It is noted that such a scintillator may be a single crystal, but may also consist of a screen with the scintillator bonded in powdery form. In such an indirect detector, the YAG crystal emits a number of photons when an electron hits the crystal, and a portion of these photons is detected by the CCD camera; in direct detectors, electrons impinge on the semiconductor chip of the CCD and generate electron/hole pairs, thereby forming the charge to be detected by the CCD chip.

The image formed on the fluorescent screen 107 and on the primary detector 151 is generally aberrated due to distortion produced by the lenses 106. To correct such distortion, multipoles 152 are used, each of which may be a magnetic multipole, an electrostatic multipole or a combination thereof. In the current case, three levels/sets of multipoles are shown; however, a smaller number may also suffice, or, in other cases, a larger number of multipoles may be necessary, in order to correct the distortions with greater accuracy.

It should be noted that FIG. 3 only shows a schematic rendition of a typical TEM, and that, in reality, a TEM will generally comprise many more deflectors, apertures, etc. Also, TEMs having correctors for correcting the aberration of the objective lens 105 are known, said correctors employing multipoles and round lenses.

Where the imaging beam impinges on the sample 111, secondary radiation is generated in the form of secondary electrons, visible (fluorescence) light, X-rays, etc. Detection and analysis of this secondary radiation can provide useful information about the sample 111. However, as is evident from FIG. 3, the vicinity of the sample 111 is rather cluttered, making it difficult to place conventional detectors here. The current invention obviates this problem, because a detector in accordance with the current invention is very small, and also relatively insensitive to electric/magnetic fields. Accordingly, FIG. 3 shows a supplementary detector 130, which is embodied as an integrated Multi-Pixel Photon Counter, connected to a variable voltage source 132 and biased in accordance with the invention so as to ensure that it operates at an acceptable (sub-threshold) saturation level.

As here depicted, the detector 130 is positioned at the side of the sample 111 distal from the gun 101. However, this is a matter of design choice, and a detector 130 may alternatively be positioned at the side of the sample 111 facing the gun 101. Furthermore, the small size of such inventive detectors 130 allows a plurality of them to be placed in the vicinity of the sample 111, if desired; in such a case, one could, for example, designate different detectors 130 to investigate different types of secondary radiation, and/or one could angularly/directionally resolve the detected secondary radiation. Yet another possibility would be to locate one or more of the detectors 130 more directly above and/or below the sample 111, placing them within (or at least very close to) the confines of the objective lens 105 and/or the projection system 106, for example.

One or more detectors 130 according to the invention could also be used to detect other types of radiation emanating from the sample 111, such as backscatter electrons, for example. As set forth above, a detector 130 according to the invention can be used to directly measure photonic radiation, or to indirectly measure particulate radiation (with the aid of an intermediary scintillator).

Embodiment 5

Figure 4:
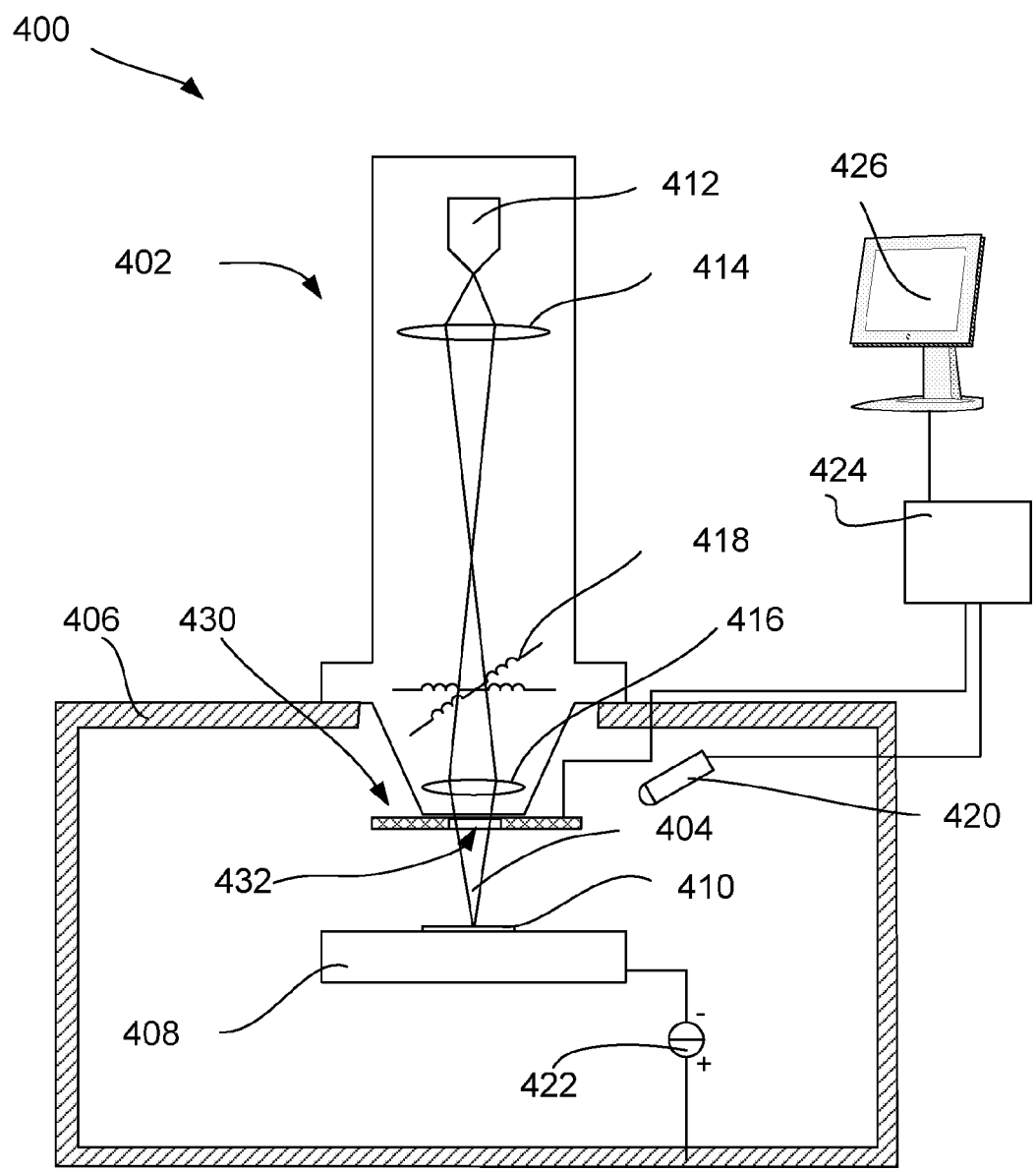
FIG. 4 shows a longitudinal cross-sectional view of a particular embodiment of another charged-particle microscope—in this specific case a SEM—according to the current invention.

FIG. 4 renders a longitudinal cross-sectional view of a particular embodiment of a SEM according to the current invention.

In FIG. 4, a SEM 400 is equipped with an electron source 412 and a SEM column (particle-optical column) 402. This SEM column 402 uses electromagnetic lenses 414, 416 to focus electrons onto a sample 410, and also employs a deflection unit 418, ultimately producing an electron beam (imaging beam) 404. The SEM column 402 is mounted onto a vacuum chamber 406 that comprises a sample stage 408 for holding a sample 410 and that is evacuated with the aid of vacuum pumps (not depicted). The sample stage 408, or at least the sample 410, may be set to an electrical potential with respect to ground, using voltage source 422.

The apparatus is further equipped with a detector 420, for detecting secondary electrons that emanate from the sample 410 as a result of its irradiation by the imaging beam 404. In prior-art SEMs, one often resorted to using a bulky Everhart-Thornley detector to fulfil thus role. However, according to the present invention, the detector 420 can be advantageously embodied as an appropriately biased Multi-Pixel Photon Counter, or as a plurality of Multi-Pixel Photon Counters placed in a distributed arrangement around the sample 410. The inventive detector 420 is small enough to be placed within the SEM column 402, and/or in very close proximity to the sample 410, if desired. A mini-scintillator can be used in conjunction with the/each Multi-Pixel Photon Counter, in order to effect the conversion of incoming secondary electrons into photonic radiation.

In addition to the detector 420, this particular set-up (optionally) comprises a sensor 430, which here takes the form of a plate provided with a central aperture 432 through which imaging beam 404 can pass. The apparatus further comprises a controller 424 for controlling inter alia the deflection unit 418, the lenses 414, 416, the detector 420 and the sensor 430, and displaying obtained information on a display unit 426.

As a result of scanning the imaging beam 404 over the sample 410, output radiation, such as secondary electrons and backscattered electrons, emanates from the sample 410. In the depicted set-up, secondary electrons are captured and registered by the detector 420, whereas backscattered electrons are detected by sensor 430. As the emanated output radiation is position-sensitive (due to said scanning motion), the obtained (detected/sensed) information is also position-dependent. The signals from the detector 420/sensor 430, either severally or jointly, are processed by the controller 424 and displayed. Such processing may include combining, integrating, subtracting, false colouring, edge enhancing, and other processing known to the skilled artisan. In addition, automated recognition processes, such as used in particle analysis, for example, may be included in such processing.

In an alternative arrangement, voltage source 422 may be used to apply an electrical potential to the sample 410 with respect to the particle-optical column 402, whence secondary electrons will be accelerated towards the sensor 430 with sufficient energy to be detected by it; in such a scenario, detector 420 can be made redundant. Alternatively, by substituting one or more of the inventive detectors 420 for the sensor 430, these detectors 420 can assume the role of detecting backscattered electrons, in which case the use of a dedicated sensor 430 can be obviated.

If desired, one can realize a controlled environment (other than vacuum) at the sample 410. For example, one can create a pressure of several mbar, as used in a so-called Environmental SEM (ESEM), and/or one can deliberately admit gases—such as etching or precursor gasses—to the vicinity of the sample 410. It should be noted that similar considerations apply to the case of a TEM, e.g. as set forth in Embodiment 4 above, whereby a so-called ETEM (Environmental TEM) can be realized, if desired.

Embodiment 6

Figure 5:
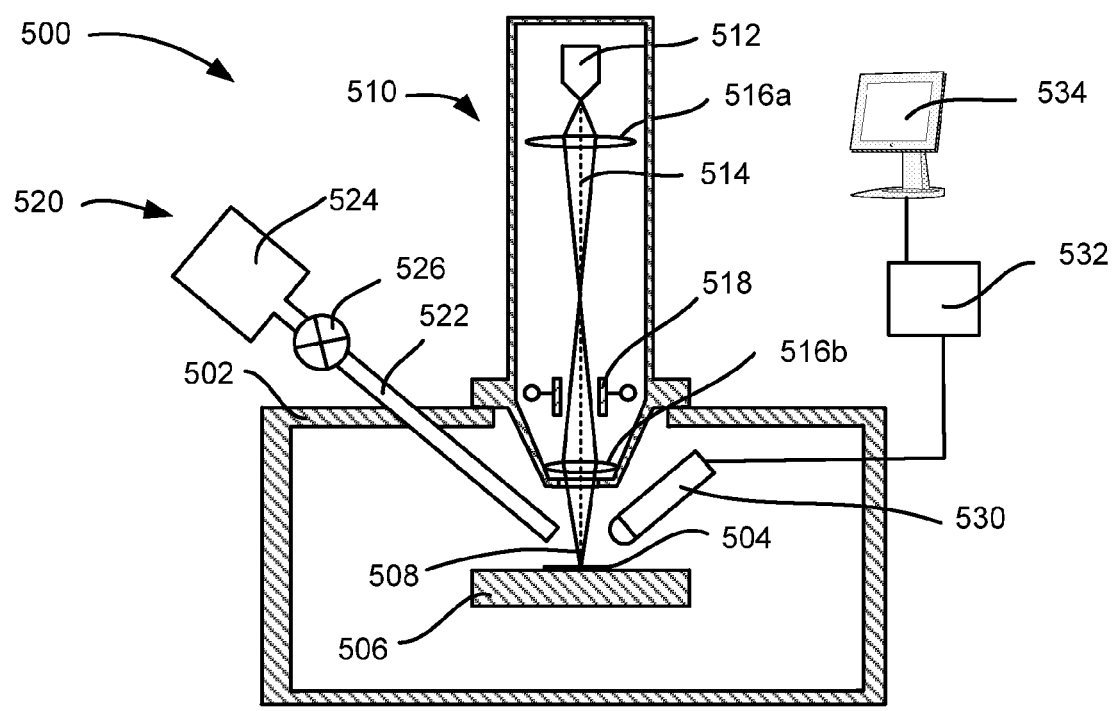
FIG. 5 shows a longitudinal cross-sectional view of a particular embodiment of yet another charged-particle microscope—in this specific case a FIB tool—according to the current invention.

FIG. 5 renders a longitudinal cross-sectional view of a particular embodiment of a FIB microscope according to the current invention.

FIG. 5 shows a FIB tool 500, which comprise a vacuum chamber 502, an ion source 512 for producing a beam of ions along an optical axis 514, and a FIB column (particle-optical column) 510. The FIB column includes electromagnetic (e.g. electrostatic) lenses 516a and 516b, and a deflector 518, and it serves to produce a focused ion beam (imaging beam) 508.

A workpiece (sample) 504 is placed on a workpiece holder (sample holder) 506. The workpiece holder 506 is embodied to be able to position the workpiece 504 with respect to the focused ion beam 508 produced by the FIB column 502.

The FIB apparatus 500 is further equipped with a Gas Injection System (GIS) 520. The GIS 520 comprises a capillary 522 though which a gas may be directed to the workpiece 504, and a reservoir 524 containing the gas (or a precursor substance used to produce the gas). A valve 526 can regulate the amount of gas directed to the workpiece 504. Such a gas may be used in depositing a (protective) layer on the workpiece 504, or to enhance a milling operation performed on the workpiece 504, for example. If desired, multiple GIS devices 520 may be employed, so as to supply multiple gases according to choice/requirement.

The FIB tool 500 is further equipped with a detector 530, which, as here embodied, is used to detect secondary radiation emanating from the sample 504 as a result of its irradiation by the ion beam 508. The signal from the detector 530 is fed to a controller 532. This controller 532 is equipped with a computer memory for storing the data derived from this signal. The controller 532 also controls other parts of the FIB, such as the lenses 516a/b, the deflector 518, the workpiece holder 506, the flow of the GIS 520 and the vacuum pumps (not depicted) serving to evacuate the chamber 502. In any case, the controller 532 is embodied to accurately position the ion beam 508 on the workpiece 504; if desired, the controller 532 may form an image of detected/processed data on monitor 524.

In analogy to the Embodiments above, the role of this detector 530 may, in accordance with the invention, be fulfilled by one or more suitably biased Multi-Pixel Photon Counters, which may be deployed in conjunction with one or more mini-scintillators, depending on the nature of the radiation to be detected.

In the present disclosure, the invention will—by way of example—often be set forth in the specific context of electron microscopes. However, such simplification is intended solely for clarity/illustrative purposes, and should not be interpreted as limiting.

As used throughout this text, the ensuing terms should be interpreted as follows:

The term "charged particle" refers to an electron or ion (generally a positive ion, such as a Gallium ion or Helium ion, for example).

The term "microscope" refers to an apparatus that is used to create a magnified image of an object, feature or component that is generally too small to be seen in satisfactory detail with the naked human eye. In addition to having an imaging functionality, such an apparatus may also have a machining functionality; for example, it may be used to locally modify a sample by removing material therefrom ("milling" or "ablation") or adding material thereto ("deposition"). Said imaging functionality and machining functionality may be provided by the same type of charged particle, or may be provided by different types of charged particle; for example, a Focused Ion Beam (FIB) microscope may employ a (focused) ion beam for machining purposes and an electron beam for imaging purposes (a so-called "dual beam" microscope), or it may perform machining with a relatively high-energy ion beam and perform imaging with a relatively low-energy ion beam. On the basis of this interpretation, tools such as the following should be regarded as falling within the scope of the current invention: electron microscopes, FIB apparatus, EBID and IBID apparatus (EBID=Electron-Beam-Induced Deposition; IBID=Ion-Beam-Induced Deposition), Critical Dimension (CD) measurement tools, lithography tools, Small Dual Beams (SDB), etc.

The term "particle-optical column" refers to a collection of electrostatic and/or magnetic lenses that can be used to manipulate a charged-particle beam, serving to provide it with a certain focus or deflection, for example, and/or to mitigate one or more aberrations therein.

The term "output radiation" encompasses any radiation that emanates from the sample as a result of its irradiation by the imaging beam. Such output radiation may be particulate and/or photonic in nature. Examples include secondary electrons, backscattered electrons, X-rays, visible fluorescence light, and combinations of these. The output radiation may simply be a portion of the imaging beam that is transmitted through or reflected from the sample, or it may be produced by effects such as scattering or ionization, for example.

The term "detector" refers to at least one detector somewhere in the charged-particle microscope. There may be several such detectors, of different types and/or in different locations. The invention aims to embody at least one such detector according to a specific form/functionality.

The term "electromagnetic" should be interpreted as encompassing various manifestations of electromagnetism. For example, an "electromagnetic" field may be electrostatic or magnetic in nature, or may involve a hybrid of electrical and magnetic aspects.

Although the present invention and its advantages have been described in detail, it should be understood that various changes, substitutions, and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We Claim as follows:

1. A method of investigating a sample using a charged-particle microscope, comprising the steps of:
    providing a charged-particle microscope having a particle-optical column;
    using the particle-optical column to direct an imaging beam of charged particles at the sample;
    irradiating the sample with the imaging beam causing a flux of output radiation to emanate from the sample;
    examining at least a portion of the output radiation using a detector; wherein
    the detector comprises a Solid State Photo-Multiplier that is connected to a power supply providing an adjustable electrical bias, the bias being altered to adjust a gain value of the Solid State Photo-Multiplier that matches the magnitude of the flux causing the Solid State Photo-Multiplier to operate below its saturation threshold to measure the flux without being impeded by saturation effects.

2. A method according to claim 1, wherein:
    the portion of the output radiation comprises particulate radiation; the method further comprising the step of:
    providing a scintillator to convert at least some of the particulate radiation into photonic radiation and to direct the photonic radiation to the Solid State Photo-Multiplier.

3. A method according to claim 2, wherein:
    the scintillator and Solid State Photo-Multiplier are sandwiched in a stacked structure with an interposed optically transparent separator layer;
    the stacked structure being partially encapsulated in a jacket of electrically insulating material leaving at least a portion of the scintillator exposed.

4. A method according to claim 1, wherein the detector is a spatially distributed structure comprising a plurality of Solid State Photo-Multipliers disposed about a point of intersection of the imaging beam and the sample.

5. A method according to claim 1, wherein the detector is located within the particle-optical column.

6. A method according to claim 5, wherein the sample holder is embodied so as to position the sample within an electromagnetic field of the particle-optical column.

7. A method according to claim 1, wherein the charged-particle microscope is selected from the group comprising a scanning electron microscope, a transmission electron microscope, a scanning transmission electron microscope, a focused ion beam tool, an electron-beam-induced deposition tool, an ion-beam-induced deposition tool, a dual-beam charged-particle microscope, a critical dimension microscope, a lithography tool, and hybrids hereof.

8. A method according to claim 1, wherein the detector is selected from the group comprising:
    a Solid-State Photo-Multiplier;
    an on-chip pixelated array of avalanche photodiodes with shared detection circuitry;
    a Multi-Pixel Photon Counter, and combinations hereof.

9. A charged-particle microscope constructed and arranged to perform a method as claimed in claim 1.

10. A method of investigating a sample using a charged-particle microscope, comprising the steps of:
    irradiating the sample with a charged particle imaging beam causing a flux of output radiation to emanate from the sample;
    examining at least a portion of said output radiation using a detector, said detector comprising a Solid State Photo-Multiplier that is connected to a power supply providing an adjustable electrical bias;
    adjusting said bias so as to adjust a gain value of the Solid State Photo-Multiplier; and
    matching said gain value to the magnitude of said flux, so as to cause the Solid State Photo-Multiplier to operate below its saturation threshold to measure said flux without being impeded by saturation effects.

11. The method according to claim 10, wherein:
    said portion of the output radiation comprises particulate radiation;
    a scintillator is employed to convert at least some of said particulate radiation into photonic radiation; and
    said photonic radiation is directed to said Solid State Photo-Multiplier.

12. The method according to claim 11, wherein:
    the scintillator and Solid State Photo-Multiplier are sandwiched in a stacked structure, with an interposed optically transparent separator layer; and
    the stacked structure is partially encapsulated in a jacket of electrically insulating material, leaving at least a portion of the scintillator exposed.

13. The method according to claim 10, wherein the detector comprises a spatially distributed structure comprising a plurality of Solid State Photo-Multipliers disposed about a point of intersection of the imaging beam and the sample.

14. The method according to claim 10, wherein the detector is located within the particle-optical column.

15. The method according to claim 10, wherein said charged-particle microscope is selected from the group comprising a scanning electron microscope, a transmission electron microscope, a scanning transmission electron microscope, a focused ion beam tool, an electron-beam-induced deposition tool, an ion-beam-induced deposition tool, a dual-beam charged-particle microscope, a critical dimension microscope, a lithography tool, and hybrids hereof.

16. The method according to claim 10, wherein said detector is selected from the group comprising:
    a Solid-State Photo-Multiplier;
    an on-chip pixelated array of avalanche photodiodes with shared detection circuitry;
    a Multi-Pixel Photon Counter, and combinations hereof.

17. A charged particle microscope, comprising:
a source of charged particles;
a charged particle lens for focusing the charged particles;
a detector for detecting emissions from a sample in response to the impact of the charged particles, the detector comprising:
   a solid state multi-pixel photon counter;
   an adjustable power supply to provide an adjustable electrical bias to adjust the gain of the multi-pixel photon counter, the gain being adjusted to operate the multi-pixel photon counter below a saturation threshold for the multi pixel photon counter to measure the emissions.

18. The charged particle microscope of claim 17 in which the multi-pixel photon counter comprises an array of Geiger mode avalanche photodiodes.

19. The charged particle microscope of claim 17 further comprising:
   a scintillator that emits light when impacted by a particle; and
   an transparent electrically insulating material positioned between the scintillator and the multi-pixel photon counter.

20. The method of claim 1 in which the detector comprises a solid state multi-pixel photon counter.

21. The method of claim 19 in which the solid state multi-pixel photon counter comprises an array of Geiger mode avalanche photodiodes.

* * * * *